(12) United States Patent
Ashida et al.

(10) Patent No.: US 7,930,021 B2
(45) Date of Patent: Apr. 19, 2011

(54) BODY COMPOSITION MEASURING APPARATUS

(75) Inventors: Tameo Ashida, Takatsuki (JP); Tadashi Koike, Kyoto (JP); Kazuya Andachi, Tokyo (JP)

(73) Assignee: Omron Healthcare Co., Ltd., Kyoto-shi (JP)

( * ) Notice: Subject to any disclaimer, the term of this patent is extended or adjusted under 35 U.S.C. 154(b) by 333 days.

(21) Appl. No.: 12/091,442

(22) PCT Filed: Oct. 11, 2006

(86) PCT No.: PCT/JP2006/320292
§ 371 (c)(1),
(2), (4) Date: Apr. 24, 2008

(87) PCT Pub. No.: WO2007/052451
PCT Pub. Date: May 10, 2007

(65) Prior Publication Data
US 2009/0247897 A1   Oct. 1, 2009

(30) Foreign Application Priority Data

Oct. 31, 2005   (JP) .................................. 2005-316948

(51) Int. Cl.
*A61B 5/05*   (2006.01)
(52) U.S. Cl. ........................................................ 600/547
(58) Field of Classification Search .................. 600/547, 600/372, 382, 384, 393; 702/19
See application file for complete search history.

(56) References Cited

U.S. PATENT DOCUMENTS

| 5,817,031 | A | * | 10/1998 | Masuo et al. | 600/547 |
| D413,536 | S | * | 9/1999 | Hirakawa et al. | D10/78 |
| D457,454 | S | * | 5/2002 | Yuan | D10/98 |
| D458,862 | S | * | 6/2002 | Yuan | D10/98 |
| 6,400,983 | B1 | * | 6/2002 | Cha | 600/547 |
| D503,119 | S | * | 3/2005 | Motomizu et al. | D10/92 |
| 7,008,350 | B1 | * | 3/2006 | Yamazaki et al. | 482/8 |

FOREIGN PATENT DOCUMENTS

| EP | 1 129 662 | 9/2001 |
| JP | 7-051242 | 2/1995 |
| JP | 11-188016 | 7/1999 |
| JP | 2003-159227 | 6/2003 |

OTHER PUBLICATIONS

International Search report mailed Jan. 16, 2007, directed at counterpart PCT application No. PCT/JP2006/320292; 1 page.
European Search Report mailed Aug. 28, 2009, directed to corresponding application No. EP 06 81 1599; 7 pages.

* cited by examiner

*Primary Examiner* — Nicholas D Lucchesi
*Assistant Examiner* — Melissa A Snyder
(74) *Attorney, Agent, or Firm* — Morrison & Foerster LLP

(57) ABSTRACT

A body composition measuring apparatus includes a right hand grip having electrodes to be contacted with the right hand of a subject, and a left hand grip having electrodes to be contacted with the left hand of the subject. The right hand grip and the left hand grip are disposed such that their respective axis lines overlap with each other on the same straight line. The left hand grip is coupled to the right hand grip in a freely movable manner such that the left hand grip can move in the axis line direction. This configuration allows a small-sized body composition measuring apparatus suitable for carrying along to be achieved.

15 Claims, 17 Drawing Sheets

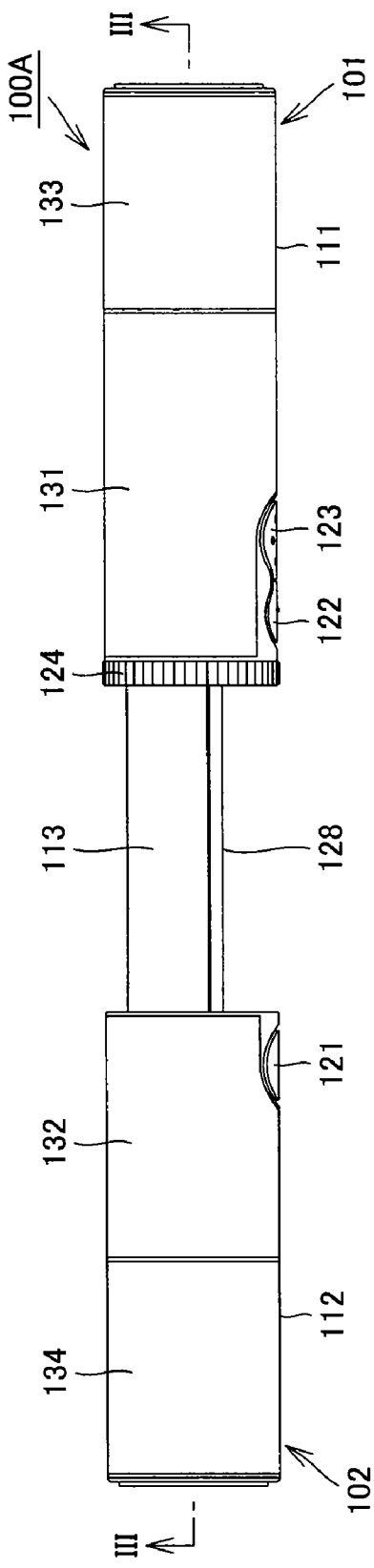

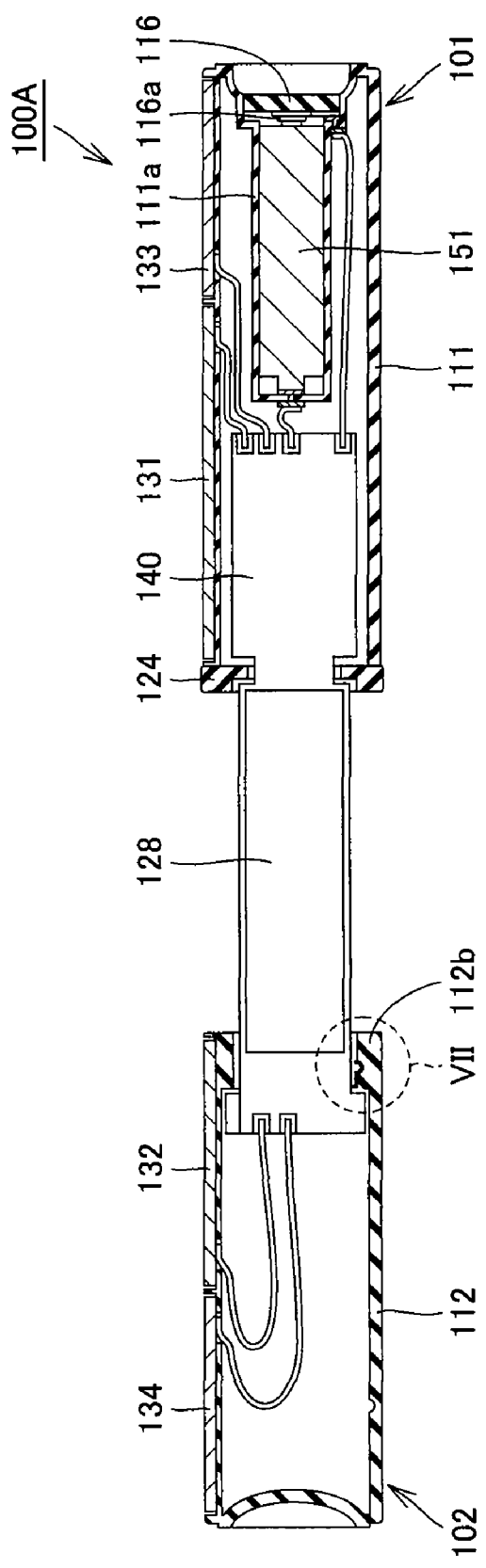

BODY COMPOSITION MEASURING APPARATUS

CROSS-REFERENCE TO RELATED APPLICATIONS

This application is a national stage application under 35 USC 371 of International Application No. PCT/JP2006/320292, filed Oct. 11, 2006, which claims the benefit of priority to Japanese Application No. 2005-316948, filed Oct. 31, 2005, the disclosures of which are hereby incorporated by reference.

TECHNICAL FIELD

The present invention relates to a body composition measuring apparatus capable of measuring a body composition of a subject by measuring an impedance of the body of the subject, and more specifically to a small-sized body composition measuring apparatus capable of being carried along.

BACKGROUND ART

Conventionally, there is known a body composition measuring apparatus that measures a body composition of a subject by measuring an impedance of the body. The body composition measuring apparatus provides useful information for health care, and has become widespread in the home and the like.

For example, as the body composition measuring apparatus capable of being carried along, a body composition measuring apparatus is disclosed in Japanese Patent Laying-Open No. 07-51242 (Patent Document 1). In the body composition measuring apparatus disclosed in Patent Document 1, a right hand grip having an electrode for a right hand and a left hand grip having an electrode for a left hand are disposed on both right and left ends, respectively, of a main body casing. By holding these electrodes with a right hand and a left hand, respectively, a body composition can be measured (conventional example 1). At this point, the right hand grip and the left hand grip are disposed spaced from each other such that the spaced distance is approximately equal to the shoulder length of the subject. In this way, consideration is given so that a proper posture for measurement is maintained.

However, with a configuration as in the foregoing conventional example 1, there is a problem that a body composition measuring apparatus becomes too large to be suitable for carrying along. To address this problem, a body composition measuring apparatus (conventional example 2) is disclosed in Patent Document 1. In this body composition measuring apparatus, guide rods are provided in the upper and lower ends of a right hand grip and a left hand grip so that the grips are each positioned to extend in the vertical direction when the subject takes a posture for measurement. Both the grips are attached to a main body casing in a freely slidable manner such that the guide rods can be contained inside the main body casing provided with a display. Thus, the outer shape of the apparatus when the apparatus is not used becomes more compact.

Patent Document 1: Japanese Patent Laying-Open No. 07-51242

DISCLOSURE OF THE INVENTION

Problems to be Solved by the Invention

However, with a configuration as in the conventional example 2, guide rods need to be provided in grips. Thus, there is a problem that the apparatus configuration becomes complicated. Further, to store the guide rods in a main body casing, the main body casing needs to be made larger than necessary. This may hinder downsizing of the apparatus.

With a configuration as in the conventional example 2, a display is exposed at all times even when an apparatus is not used. Therefore, there is also a problem that the display can be broken when the apparatus is being carried.

The present invention has been made in view of the above problems, and has an object of providing a small-sized body composition measuring apparatus that is suitable for carrying along.

Means for Solving the Problems

A body composition measuring apparatus according to the present invention includes, in a portable apparatus body, a first electrode to be contacted with one hand of a subject, a second electrode to be contacted with the other hand of the subject, and a measurement portion that measures an impedance of a body of the subject using the first electrode and the second electrode. The apparatus body includes a cylindrical first grip having the first electrode and a cylindrical second grip having the second electrode, and the first grip and the second grip are disposed such that respective axis lines thereof overlap with each other on the same straight line. The second grip is coupled, so as to be movable in a direction of the axis line thereof, to the first grip in a freely movable manner.

This configuration enables a small-sized body composition measuring apparatus having a simplified configuration to be obtained.

In the foregoing body composition measuring apparatus according to the present invention, it is preferable that the second grip is coupled to the first grip in a freely movable manner so as to be movable between a first position where measurement by the measurement portion is possible and a second position where measurement by the measurement portion is impossible. In this case, it is preferable that a display capable of displaying a body composition based on a measurement result measured by the measurement portion is exposed in a state where the second grip is at the first position, and covered with at least one of the first grip and the second grip in a state where the second grip is at the second position.

A "position where measurement by the measurement portion is possible" herein refers to a position where the second grip is actually disposed when an impedance is measured, and a "position where measurement by the measurement portion is impossible" refers to a position that is most suitable for carrying the apparatus among positions that the second grip can take when measurement of an impedance is not performed. Hereinafter, a "position where measurement by the measurement portion is possible" will be referred to as a "measurable position" and a state where the second grip is disposed at this position will be referred to as a "measurable state". A "position where measurement by the measurement portion is impossible" will be referred to as a "storage position" and a state where the second grip is disposed at this position will be referred to as a "storage state".

With this configuration, the display is exposed in the measurable state, allowing the subject to visually recognize the measurement result. Also, the display is covered in the storage state, preventing the display from being broken. Therefore, a body composition measuring apparatus that is suitable for carrying and in which a display will not be broken can be obtained.

In the foregoing body composition measuring apparatus according to the present invention, it is preferable that the first position is a position where the second grip is, in the movable range thereof, remotest from the first grip, and it is also preferable that the second position is a position where the second grip is, in the movable range thereof, closest to the first grip. In this case, more preferably, the length in the foregoing axis line direction of the apparatus body when the second grip is at the second position is smaller than the length in the foregoing axis line direction of the apparatus body when the second grip is at the first position.

This configuration causes, in the measurable state, the first grip and the second grip to be disposed spaced at a distance approximately equal to the shoulder length of the subject, allowing a proper posture for measurement to be maintained. It also allows, in the storage state, the outer shape of the apparatus to be made shorter in the length direction. Therefore, a small-sized body composition measuring apparatus suitable for carrying along can be obtained.

In the foregoing body composition measuring apparatus according to the present invention, it is preferable that an engaging mechanism capable of engaging the second grip at the first position and at the second position is further provided.

This configuration allows the measurable state where the second grip is at the measurable position and the storage state where the second grip is at the storage position to be maintained by the engaging mechanism. Therefore, a body composition measuring apparatus that can be easily handled can be achieved.

In the foregoing body composition measuring apparatus according to the present invention, it is preferable that a detection portion that detects whether the second grip is at the first position is further included. In this case, it is preferable that when it is detected by the detection portion that the second grip is at the first position, power is configured to be supplied to the measurement portion.

This configuration can eliminate the need to press a power supply button. Therefore, a body composition measuring apparatus that can be easily handled can be achieved.

In the foregoing body composition measuring apparatus according to the present invention, it is preferable that when the power is supplied to the measurement portion, measurement by the measurement portion is started immediately or after the lapse of a predetermined time.

With this configuration, a measuring start button need not be provided separately and independently, and therefore the apparatus configuration can be simplified. This also eliminates the need to press a power supply button. Thus, a small-sized body composition measuring apparatus that can be easily handled can be achieved.

In the foregoing body composition measuring apparatus according to the present invention, it is preferable that a detection portion that detects whether the second grip is at the first position is further included. In this case, it is preferable that when it is detected by the detection portion that the second grip is not at the first position, the power supply to the measurement portion is configured to be stopped.

With this configuration, the need to press a power supply button can be eliminated, and forgetting to turn off the power can be prevented. Therefore, a body composition measuring apparatus that can be easily handled can be achieved.

Effects of the Invention

According to the present invention, a small-sized body composition measuring apparatus suitable for carrying along can be obtained.

BRIEF DESCRIPTION OF THE DRAWINGS

FIG. 2B is a top view showing the appearance of the body composition measuring apparatus in the measurable state shown in FIG. 1.

FIG. 3 is a cross-sectional view along the line III-III shown in FIGS. 2B and 2D of the body composition measuring apparatus in Embodiment 1 of the present invention.

DESCRIPTION OF THE REFERENCE SIGNS

Figure 1:
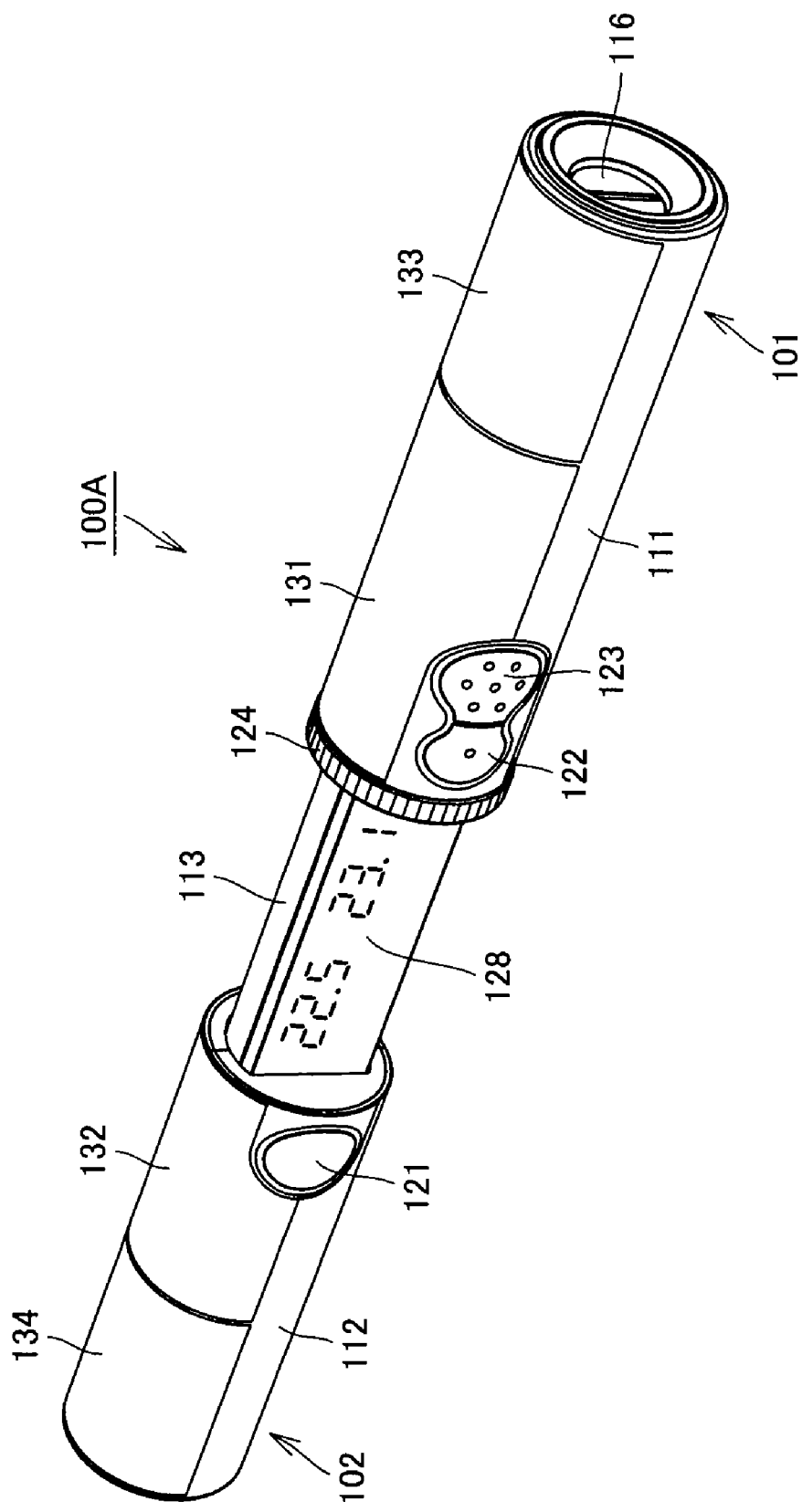
FIG. 1 is a perspective view showing the appearance of a body composition measuring apparatus in the measurable state in Embodiment 1 of the present invention.

10 Subject, 11 Right hand, 12 Left hand, 100A, 100B Body composition measuring apparatus, 101 Right hand grip, 102 Left hand grip, 111 Right casing, 111a Battery chamber, 112a Concave, 112b Stopper, 112c Concave, 112 Left casing, 113 Central part casing, 116 Cover, 116a Spring, 120 Operating portion, 121 Power supply button, 122 Setting button, 123 Measuring start button, 124 Up/down dial, 125 Setting button, 126 Up button, 127 Down button, 128 Display, 131 to 134 Electrode, 140 Circuit board, 141 Micon, 142 Impedance measurement portion, 143 Body composition calculation portion, 144 Internal memory, 148 Switching unit, 148a Switch, 149 Plate spring, 149a Elastic portion, 149b Engaging portion, 151 Battery, 152 High-frequency constant current generating circuit, 153 Voltage measuring circuit

BEST MODES FOR CARRYING OUT THE INVENTION

Preferred embodiments of the present invention will be described in detail below with reference to the accompanying drawings. Regarding the embodiments to be described below, it should be noted that the same components are denoted by the same reference numerals in the drawings, and the description thereof is not repeated.

Embodiment 1

FIG. 1 is a perspective view showing the appearance of a body composition measuring apparatus in the measurable state in Embodiment 1 of the present invention. FIGS. 2A to 2D are a front view, a top view, a rear view, and a right side view, respectively, showing the appearance of the body composition measuring apparatus in the measurable state shown in FIG. 1. With reference to these figures, the appearance configuration in the measurable state of the body composition measuring apparatus in the present embodiment is first described.

As shown in FIGS. 1 and 2A to 2D, a body composition measuring apparatus 100A in the present embodiment has a substantially cylindrical outer shape, and includes a right hand grip 101 to be held with a right hand in the right end and a left hand grip 102 to be held with a left hand in the left end. In body composition measuring apparatus 100A in the present embodiment, right hand grip 101 is a first grip and left hand grip 102 is a second grip.

A casing configuring the outer shell of the apparatus body of body composition measuring apparatus 100A is constituted by a right casing 111, a left casing 112, and a central part casing 113. Among these casings, right casing 111 and left casing 112 are each formed of a closed-end cylindrical member having one end being opened and the other end being closed. Right casing 111 and left casing 112 are disposed such that their respective opened surfaces face each other and their respective axis lines overlap with each other on the same straight line. Central part casing 113 is disposed between right casing 111 and left casing 112 so as to bridge right casing 111 and left casing 112, and a display 128 is provided on the front surface of central part casing 113. Display 128 is a display for displaying a body composition and the like measured by this body composition measuring apparatus 100A. Note that a liquid crystal display (LCD) or the like is utilized as display 128.

Electrodes 131 and 133 are provided at predetermined positions on the outer surface of right casing 111. In these electrodes 131 and 133, electrode 131 positioned on the central part side of body composition measuring apparatus 100A is an electrode for measuring voltage during impedance measurement, and electrode 133 positioned on the right end side of body composition measuring apparatus 100A is an electrode for applying an electric current during impedance measurement. These electrodes 131 and 133 are first electrodes to be contacted with the inside of the right hand of the subject.

Electrodes 132 and 134 are provided at predetermined positions on the outer surface of left casing 112. In these electrodes 132 and 134, electrode 132 positioned on the central part side of body composition measuring apparatus 100A is an electrode for measuring voltage during impedance measurement, and electrode 134 positioned on the left end side of body composition measuring apparatus 100A is an electrode for applying an electric current during impedance measurement. These electrodes 132 and 134 are second electrodes to be contacted with the inside of the left hand of the subject.

A power supply button 121 for tuning power on/off is provided in a portion adjacent to display 128 of left casing 112. Provided in a portion adjacent to display 128 of right casing 111 are a setting button 122 for performing various settings and a measuring start button 123 for providing an instruction for starting measurement. Further, provided at the end on the central part side of right casing 111 adjacent to display 128 is an up/down dial 124 for selecting a value to be inputted, e.g., at the time of setting personal data. This up/down dial 124 is provided rotatably around the axis line of cylindrical right casing 111. These power supply button 121, setting button 122, measuring start button 123, and up/down dial 124 constitute an operating portion 120 for receiving operations of the subject (see FIG. 8).

Figure 2A:
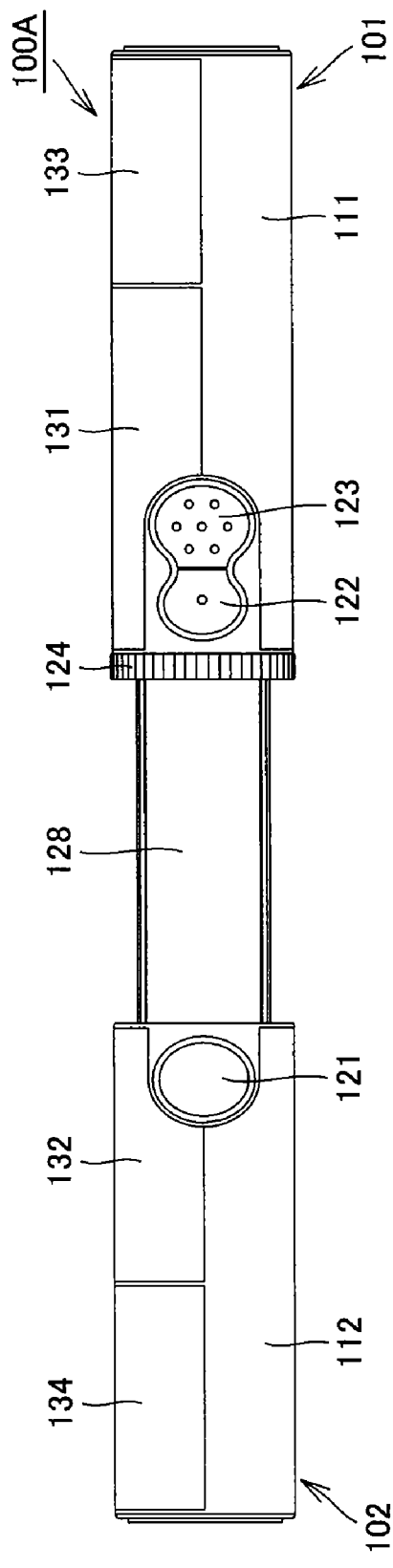
FIG. 2A is a front view showing the appearance of the body composition measuring apparatus in the measurable state shown in FIG. 1.
Figure 2C:
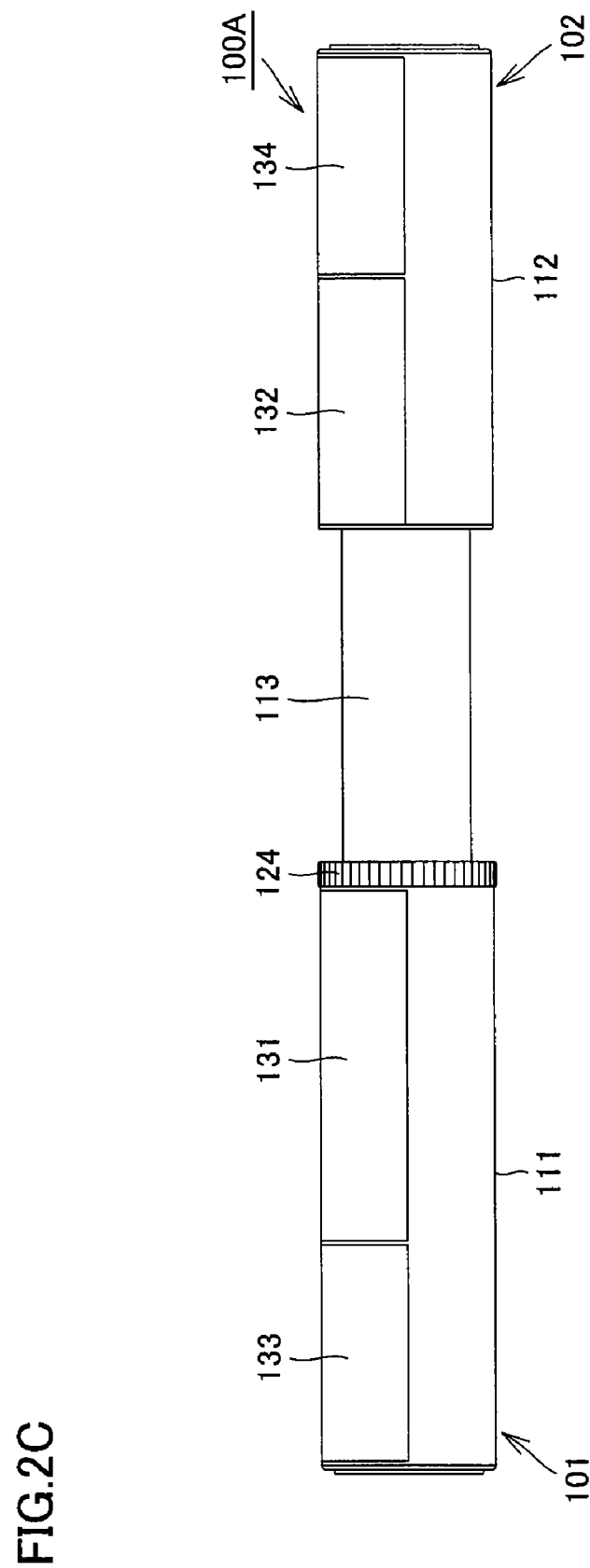
FIG. 2C is a rear view showing the appearance of the body composition measuring apparatus in the measurable state shown in FIG. 1.
Figure 2D:
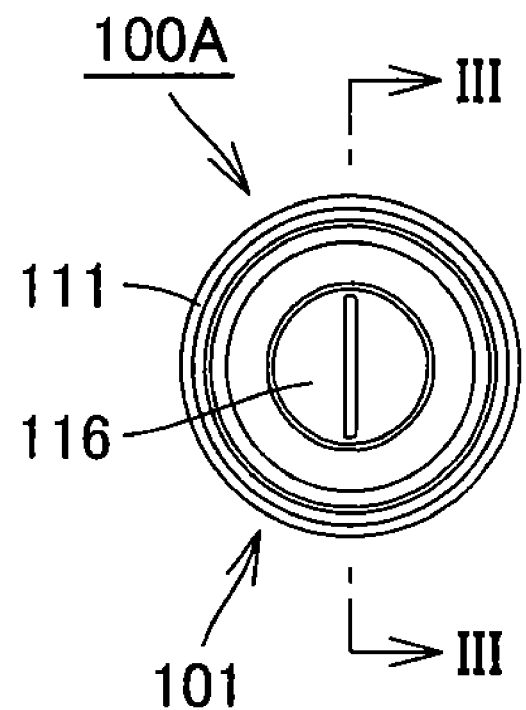
FIG. 2D is a right side view showing the appearance of the body composition measuring apparatus in the measurable state shown in FIG. 1.

As shown in FIGS. 1 and 2D, a cover 116 is attached to an end surface of right casing 111, which is the right side end surface of body composition measuring apparatus 100A, in a detachable manner. This cover 116, in a state of being attached to right casing 111, closes a battery chamber 111a (see FIG. 3) for containing a battery 151 (see FIG. 3) to be described later.

FIG. 3 is a cross-sectional view of the body composition measuring apparatus in the present embodiment taken along the line III-III shown in FIGS. 2B and 2D. With reference to this figure, an internal configuration of the body composition measuring apparatus in the present embodiment will be described next.

As described above, in body composition measuring apparatus 100A in the present embodiment, both right casing 111 constituting right hand grip 101 and left casing 112 constituting left hand grip 102 are formed of cylindrical members. As shown in FIG. 3, various parts constituting body composition measuring apparatus 100A are contained inside these right and left casings 111 and 112 and central part casing 113.

Specifically, as shown in FIG. 3, a circuit board 140 is disposed inside central part casing 113 that is disposed so as to bridge right casing 111 and left casing 112. The right end of this circuit board 140 is contained inside right casing 111, and the left end of circuit board 140 is contained inside left casing 112. Various circuits to be described later are formed by mounting various electronic parts on this circuit board 140. In addition, display 128 is provided on this circuit board 140.

Provided inside right casing 111 is a battery chamber 111a, and battery 151 is contained inside battery chamber 111a. Battery 151 is biased and held by a spring 116a attached to the back surface of cover 116. An electrode of battery 151 is electrically connected to circuit board 140 with a lead wire. Lead wires are connected to the back surfaces of electrodes 131 and 133 provided at predetermined positions of the outer surface of right casing 111 and the back surfaces of electrodes 132 and 134 provided at predetermined positions of the outer surface of left casing 112 by soldering and the like. These electrodes are electrically connected to circuit board 140 with these lead wires.

In body composition measuring apparatus 100A in the present embodiment, left casing 112 constituting left hand grip 102 is coupled to right casing 111 constituting right hand grip 101 in a relatively freely movable manner. Specifically, the right end of central part casing 113 provided to bridge right casing 111 and left casing 112 is fixed to right casing 111, and the left end of central part casing 113 is inserted into left casing 112 and is configured to be movable along the axis line direction of left casing 112 inside left casing 112. Accordingly, the movement direction of left casing 112 with respect to right casing 111 is the axis line direction of left casing 112. Inside left casing 112, movement of the left end of central part casing 113 is restricted by a stopper 112b provided on the inner peripheral surface of the end of left casing 112 on the central part side of body composition measuring apparatus 100A. This prevents central part casing 113 from being detached from left casing 112.

By employing the configuration described above, body composition measuring apparatus 100A in the present embodiment can be in a measurable state where left casing 112 is remotest from right casing 111 in the movable range, and can also be in a storage state where left casing 112 is closest to right casing 111 in the movable range. In the following, a case of body composition measuring apparatus 100A in the storage state will be described in detail.

Figure 4:
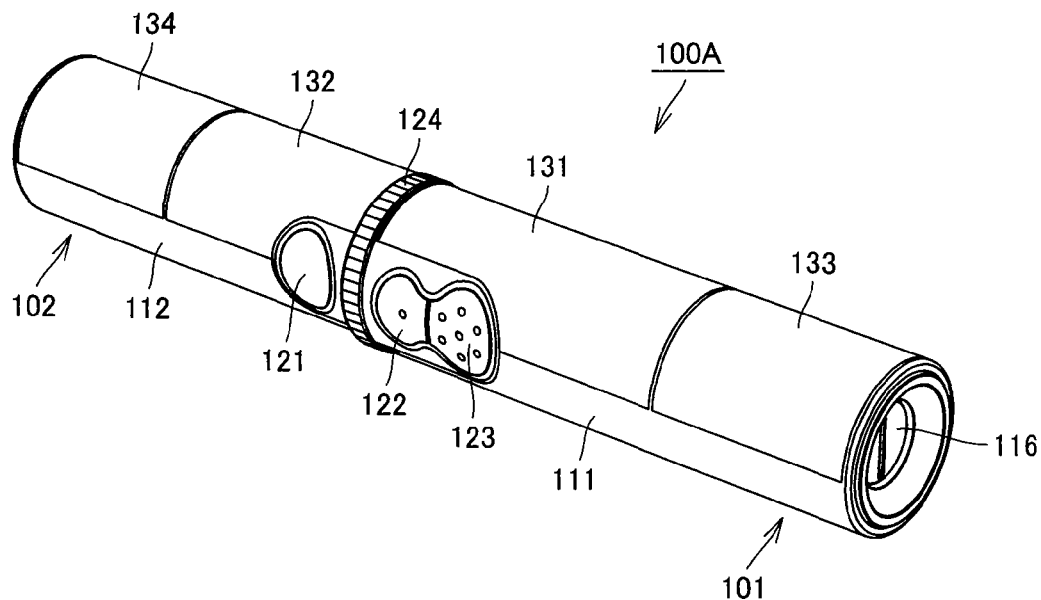
FIG. 4 is a perspective view showing the appearance of the body composition measuring apparatus in the storage state in Embodiment 1 of the present invention.
Figure 5:
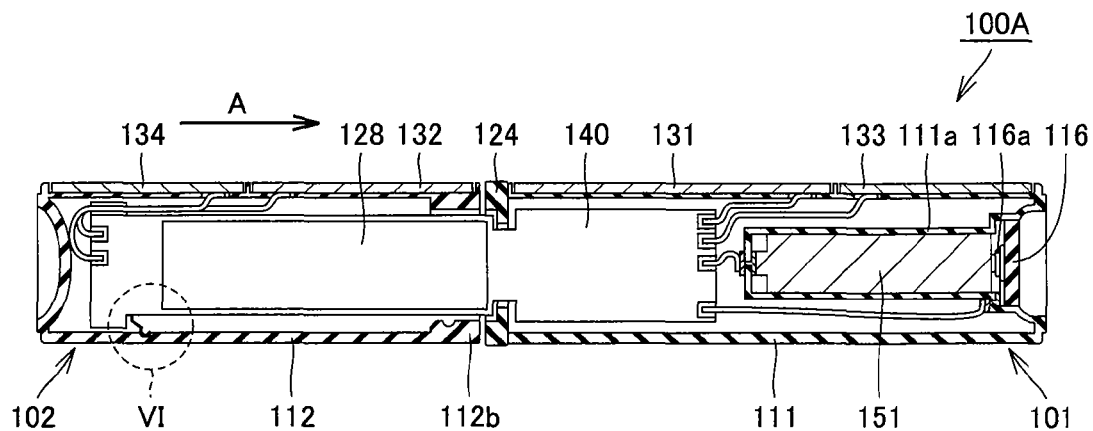
FIG. 5 is a cross-sectional view of the body composition measuring apparatus in the storage state in Embodiment 1 of the present invention.

FIG. 4 is a perspective view showing the appearance of the body composition measuring apparatus in the storage state in the present embodiment. FIG. 5 is a cross-sectional view of the body composition measuring apparatus in the storage state of the present embodiment.

As shown in FIGS. 4 and 5, in the storage state, right casing 111 constituting right hand grip 101 and left casing 112 constituting left hand grip 102 are disposed to be in contact with each other. This causes display 128 to be in a state of being covered with left casing 112. Specifically, as shown in FIG. 5, by slidingly moving left casing 112 in the arrow A direction in the figure, display 128 exposed in the measurable state is contained inside left casing 112 to be covered with left casing 112.

Employing such a configuration as described above enables display 128 to be exposed in the measurable state, allowing the subject to visually recognize the measurement result. It also enables display 128 to be covered with left hand grip 102 in the storage state, preventing display 128 from being broken. Therefore, a body composition measuring apparatus that is suitable for carrying along and in which a display will not be broken can be obtained.

In the measurable state, right hand grip 101 and left hand grip 102 are disposed spaced at a distance approximately equal to the shoulder length of the subject, allowing a proper posture for measurement to be maintained. In the storage state, the length in the axis line direction is made short as compared with the measurable state, allowing the apparatus to take a compact form. Therefore, a small-sized body composition measuring apparatus suitable for carrying can be obtained.

Body composition measuring apparatus 100A in the present embodiment has an engaging mechanism so that left casing 112 can be engaged at the position in each of the measurable state and the storage state described above. This engaging mechanism is provided so as to maintain each state so that stable measurement is possible in the measurable state, and that the display is reliably protected in the storage state. This engaging mechanism will be described in detail below.

Figure 6A:
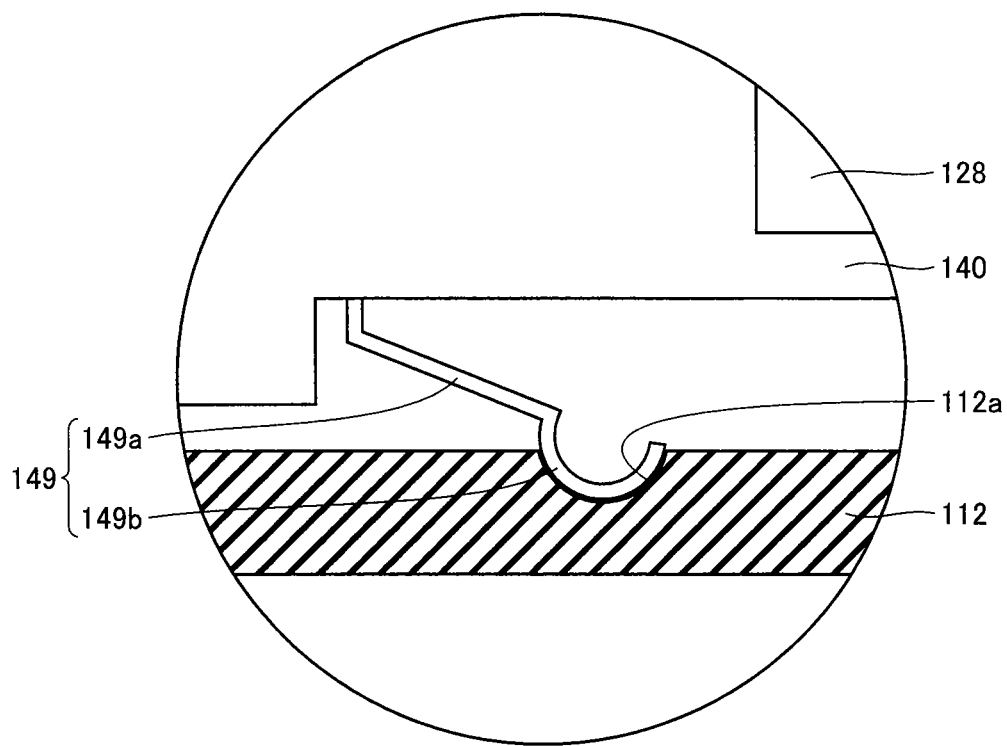
FIG. 6A is an enlarged cross-sectional view of an area VI shown in FIG. 5 in the storage state.
Figure 6B:
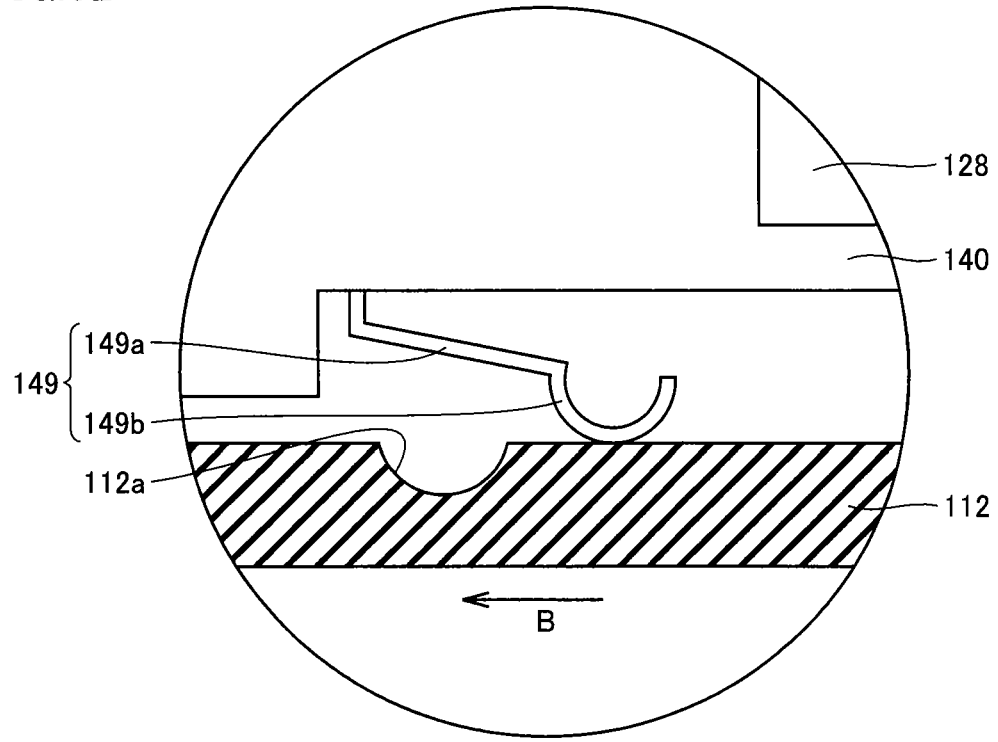
FIG. 6B is an enlarged cross-sectional view of the area VI shown in FIG. 5 immediately after the storage state is released.
Figure 7A:
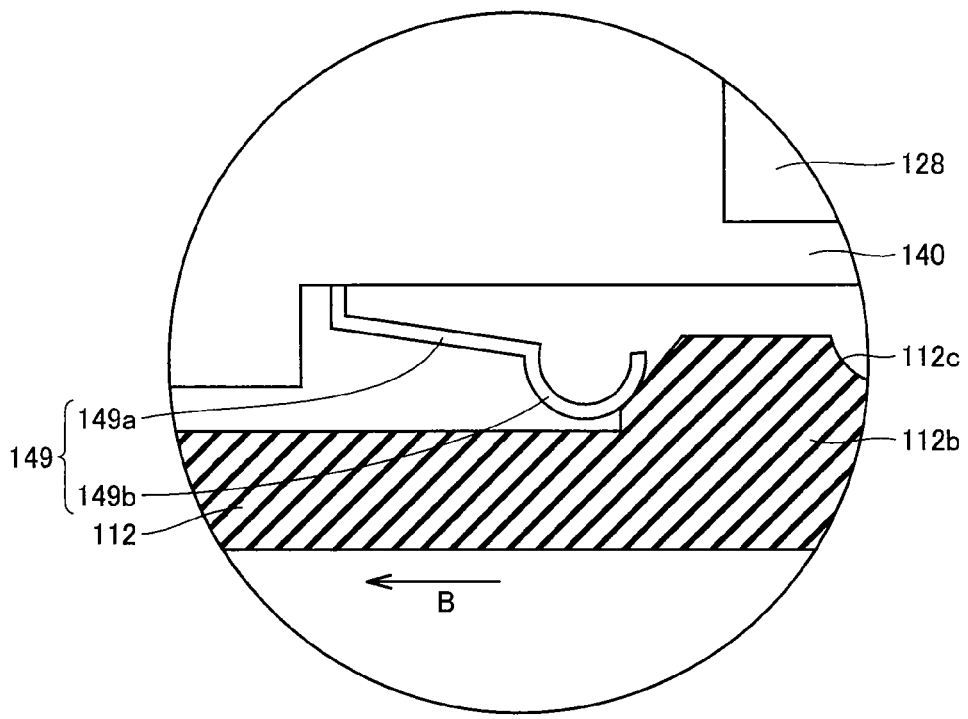
FIG. 7A is an enlarged cross-sectional view of an area VII shown in FIG. 3 immediately before the measurable state is established.
Figure 7B:
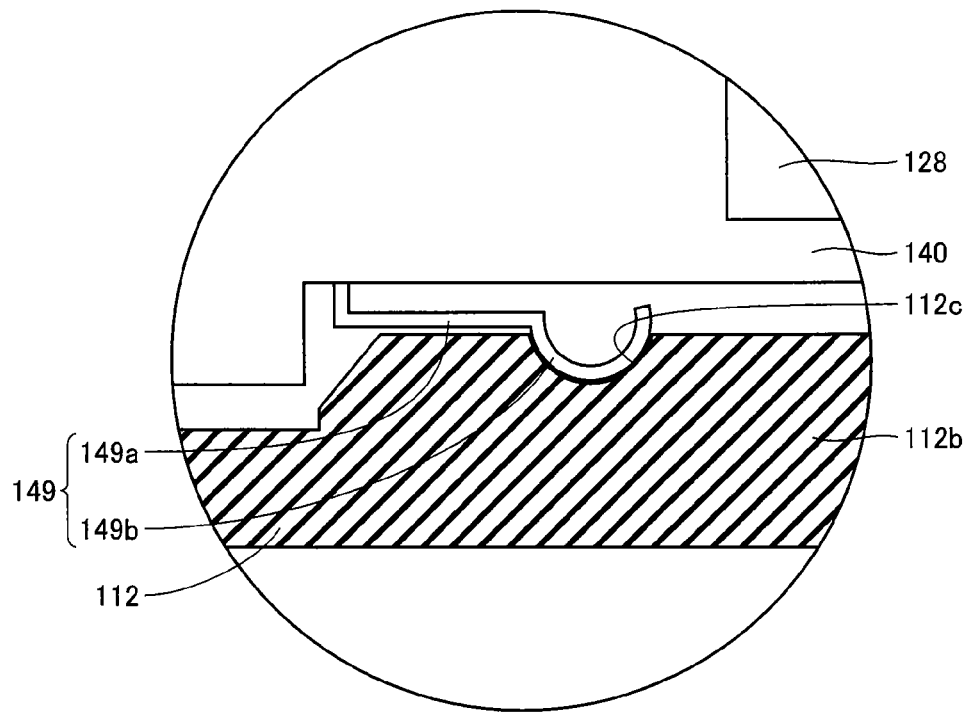
FIG. 7B is an enlarged cross-sectional view of the area VII shown in FIG. 3 when the measurable state has been established.

FIGS. 6A and 6B are enlarged cross-sectional views of an area VI shown in FIG. 5, where FIG. 6A shows the area in the storage state, and FIG. 6B shows the area immediately after the storage state is released. FIGS. 7A and 7B are enlarged cross-sectional views of an area VII shown in FIG. 3, where FIG. 7A shows the area immediately before the measurable state is established, and FIG. 7B shows the area when the measurable state has been established.

As shown in FIGS. 6A, 6B, 7A, and 7B, plate spring 149 as the engaging mechanism is attached at a predetermined position on circuit board 140. Plate spring 149 includes an elastic portion 149a extending linearly and an engaging portion 149b that is positioned at the tip of elastic portion 149a and has a curved shape. Plate spring 149 is attached to circuit board 140 so as to exert biasing force toward the outside of circuit board 140.

On the other hand, as shown in FIGS. 6A and 6B, a concave 112a that can receive engaging portion 149b of plate spring 149 is provided at a predetermined position on the inner peripheral surface of left casing 112. As shown in FIG. 6A, with engaging portion 149b of plate spring 149 fixed into this concave 112a, engaging force acts between circuit board 140 and left casing 112 due to biasing force of elastic portion 149a. As a result, the movement of left casing 112 is limited. Accordingly, the storage state shown in FIG. 5 is maintained.

However, as shown in FIG. 6B, when force is applied to left casing 112 in the arrow B direction in the figure by the subject, left casing 112 slidingly moves against the engaging force described above made by plate spring 149 and concave 112a. This causes engaging portion 149b of plate spring 149 to be disengaged from concave 112a. Thus, the storage state is released, thereby realizing smooth movement of left casing 112 with respect to right casing 111.

As shown in FIGS. 7A and 7B, a concave 112c that can receive engaging portion 149b of plate spring 149 is provided at a predetermined position of stopper 112b of left casing 112. By the foregoing operation by the subject, left casing 112 further moves in the arrow B direction shown in FIG. 7A. When engaging portion 149b of plate spring 149 reaches stopper 112b, engaging portion 149b of plate spring 149 gets over a tapered surface provided on stopper 112b. Then, as shown in FIG. 7B, engaging portion 149b of plate spring 149 is fixed into concave 112c provided in stopper 112b, and engaging force acts between circuit board 140 and left casing 112 due to biasing force of elastic portion 149a. As a result, the movement of left casing 112 is limited. Accordingly, the measurable state shown in FIG. 3 is maintained.

Configuring the apparatus in this way enables the measurable state where left hand grip 102 is at the measurable position and the storage state where left hand grip 102 is at the storage position to be maintained. Therefore, a body composition measuring apparatus that can be easily handled can be obtained.

Figure 8:
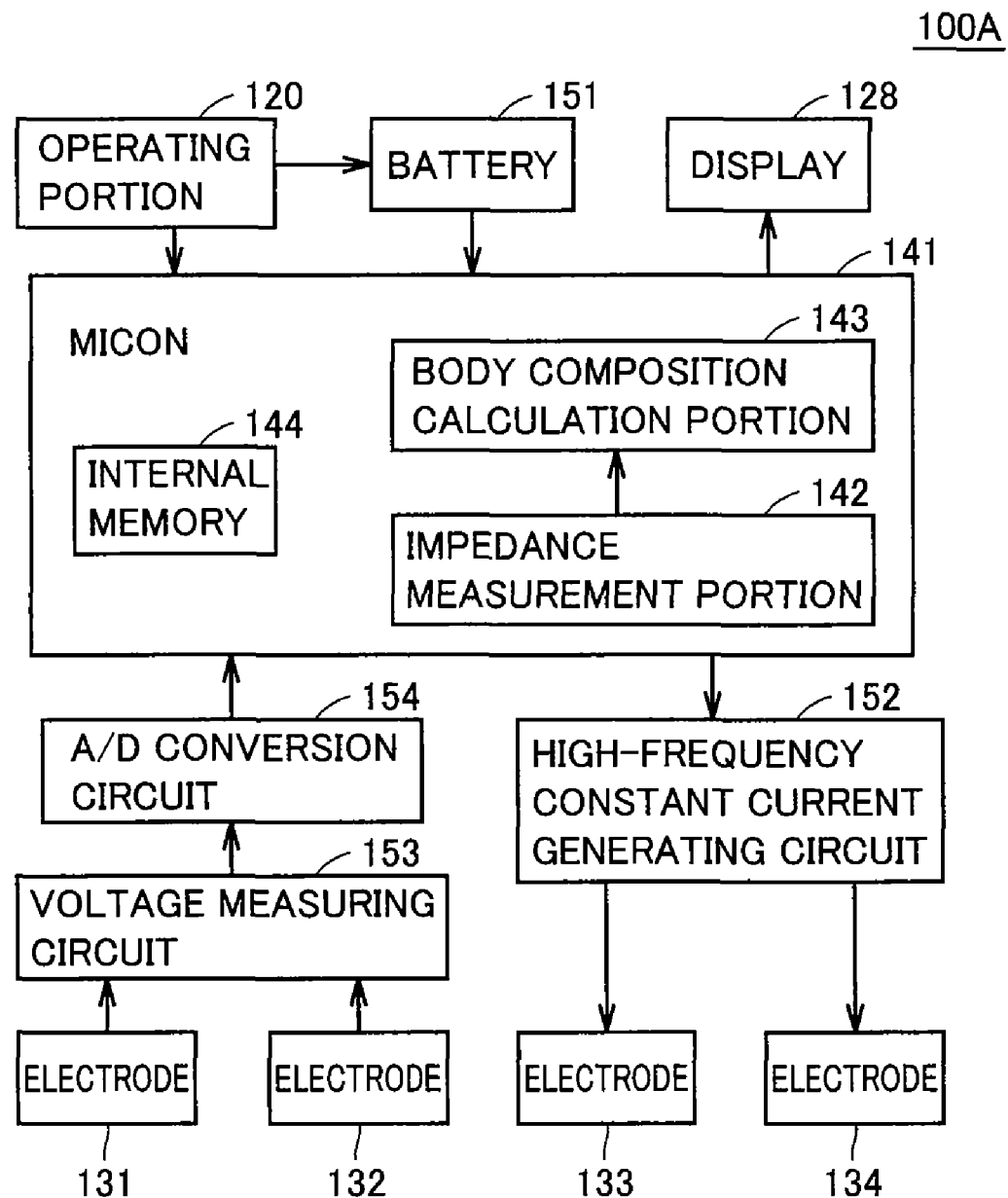
FIG. 8 shows functional blocks of the body composition measuring apparatus in Embodiment 1 of the present invention.

FIG. 8 shows functional blocks of the body composition measuring apparatus in the present embodiment. With reference to this figure, the functional blocks of the body composition measuring apparatus in the present embodiment will be described next.

As shown in FIG. 8, body composition measuring apparatus 100A in the present embodiment includes, in addition to electrodes 131 to 134, display 128, operating portion 120, and battery 151, a microcomputer (micon) 141 for performing control over entire body composition measuring apparatus 100A and performing processes such as various operations, a high-frequency constant current generating circuit 152 that generates a high-frequency constant current of a predetermined frequency, a voltage measuring circuit 153 that measures voltage information obtained from electrodes 131 and 132 for voltage measurement, and an analog/digital (A/D) conversion circuit 154 for converting the voltage information obtained from voltage measuring circuit 153 from analog signals to digital signals. Micon 141 includes an impedance measurement portion 142 that measures an impedance of a body from voltage information in digital signals, a body composition calculation portion 143 that calculates a body composition by computing the obtained impedance, and an internal memory 144 for storing various control programs and the like.

It should be noted that examples of the body composition that can be measured by body composition measuring apparatus 100A of the present embodiment include an amount of body fat, a lean body mass, a muscle mass, a bone mass, a percent of body fat, a muscle percentage, and a visceral fat level. These body compositions are calculated from impedance values of a body obtained in impedance measurement portion 142 described above and personal data such as height, body weight, age, and gender of a subject stored in the internal memory using a known method by body composition calculation portion 143.

Figure 9:
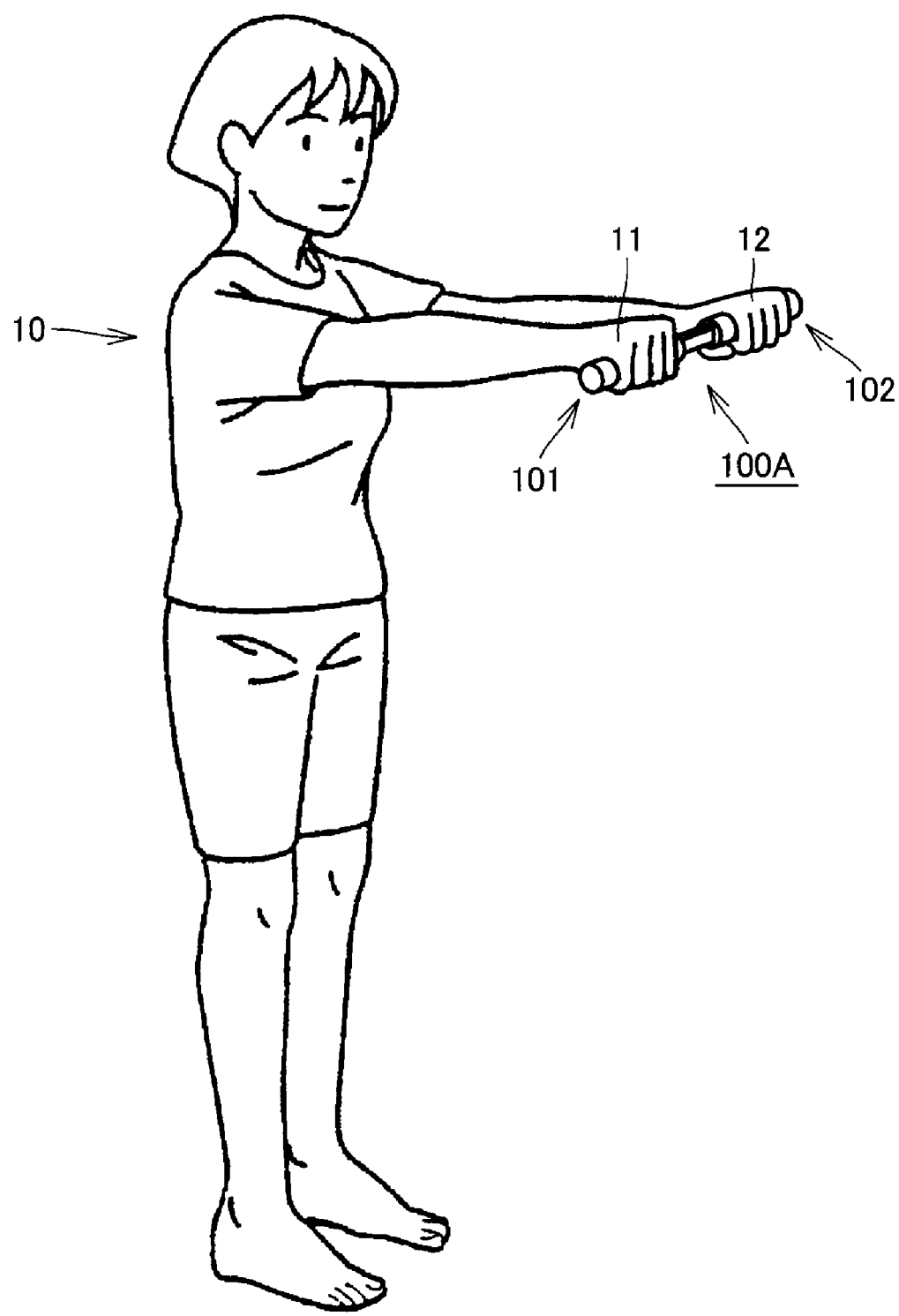
FIG. 9 shows a posture for measurement taken when a subject measures a body composition using the body composition measuring apparatus in Embodiment 1 of the present invention.

FIG. 9 shows a posture for measurement taken when the subject measures a body composition using the body composition measuring apparatus in the present embodiment. As shown in FIG. 9, a subject 10 holds right hand grip 101 and left hand grip 102 of body composition measuring apparatus 100A with a right hand 11 and with a left hand 12, respectively, while taking an upright posture. At this point, the elbows of both the arms are extended, and both the arms are maintained at a height approximately equal to that of the shoulder so that body composition measuring apparatus 100A is positioned in front of the body, and that the arms and the trunk are approximately perpendicular to each other.

Figure 10:
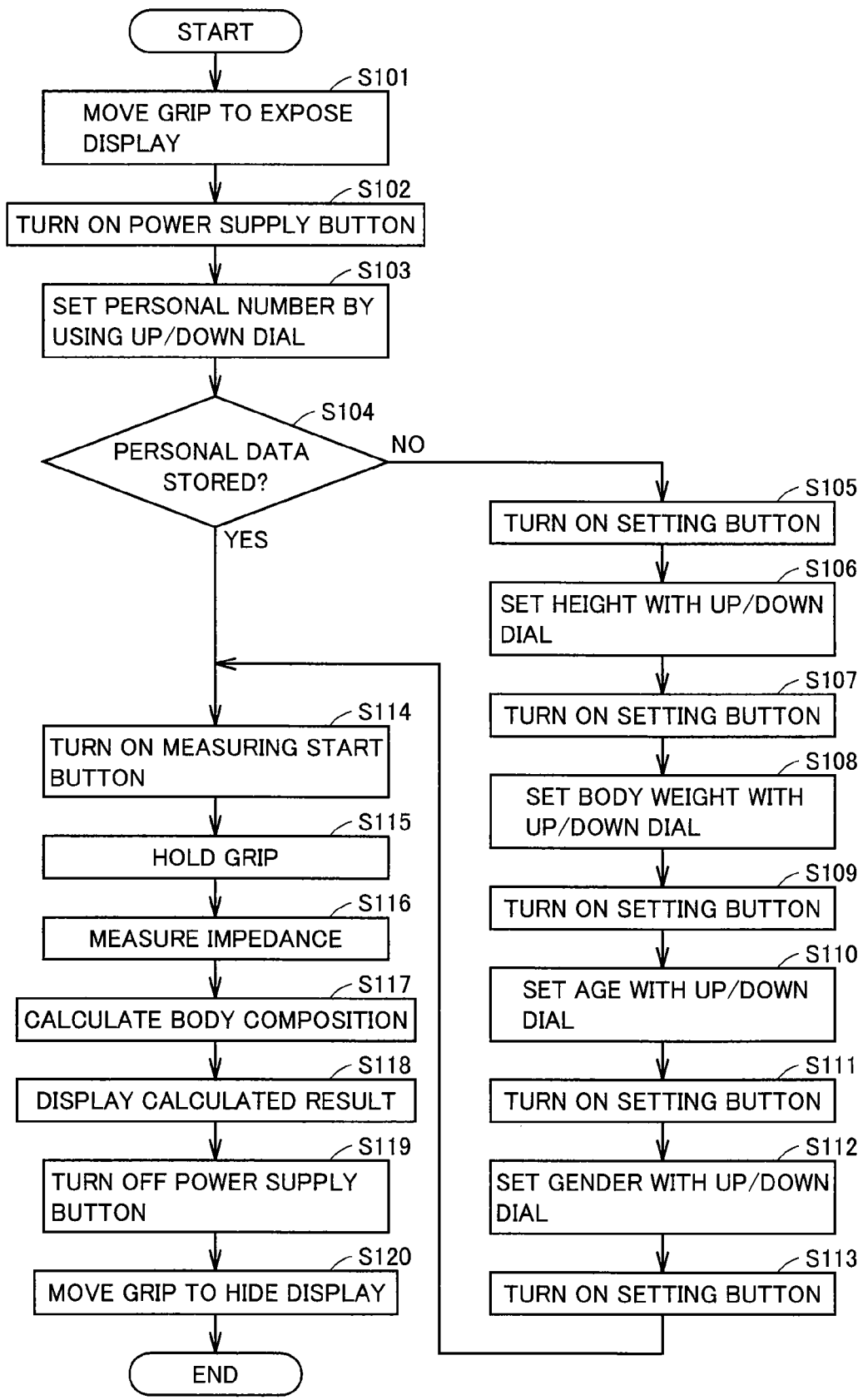
FIG. 10 is a flowchart in a case of measuring a body composition using the body composition measuring apparatus in Embodiment 1 of the present invention.

FIG. 10 is a flowchart in a case of measuring a body composition using the body composition measuring apparatus in the present embodiment. With reference to this figure, the flow when a body composition is measured will be described below.

As shown in FIG. 10, when a body composition is measured, first in step S101, left hand grip 102 is slidingly moved with respect to right hand grip 101 to expose display 128, thereby establishing the measurable state. Next, in step S102, power supply button 121 is turned on. In step S103, a personal number with which personal data is recorded is set by using up/down dial 124. At this point, it is determined in step S104 whether the personal data is recorded with the personal number. If the personal data is not stored with the personal number, then the process proceeds to step S105, and setting button 122 is pressed down. Thereafter, in steps S106 to S113, up/down dial 124 and setting button 122 are operated to set personal data such as height, body weight, age, and gender, in succession.

If personal data is stored in step S104 or when setting of personal data is completed in steps S106 to S113, then the process proceeds to step S114, and measuring start button 123 is pressed down. Thereafter, in step S115, both grips 101 and 102 are held in the posture shown in FIG. 9. In step S116, an impedance is measured; in step S117, a body composition is calculated; and in step S118, the calculated result of the body composition is displayed on display 128. When the measurement is completed, in step S119, power supply button 121 is pressed down to turn off the power, and in step 120, left hand grip 102 is slidingly moved with respect to right hand grip 101 to hide display 128, thereby establishing the storage state.

Embodiment 2

Figure 11:
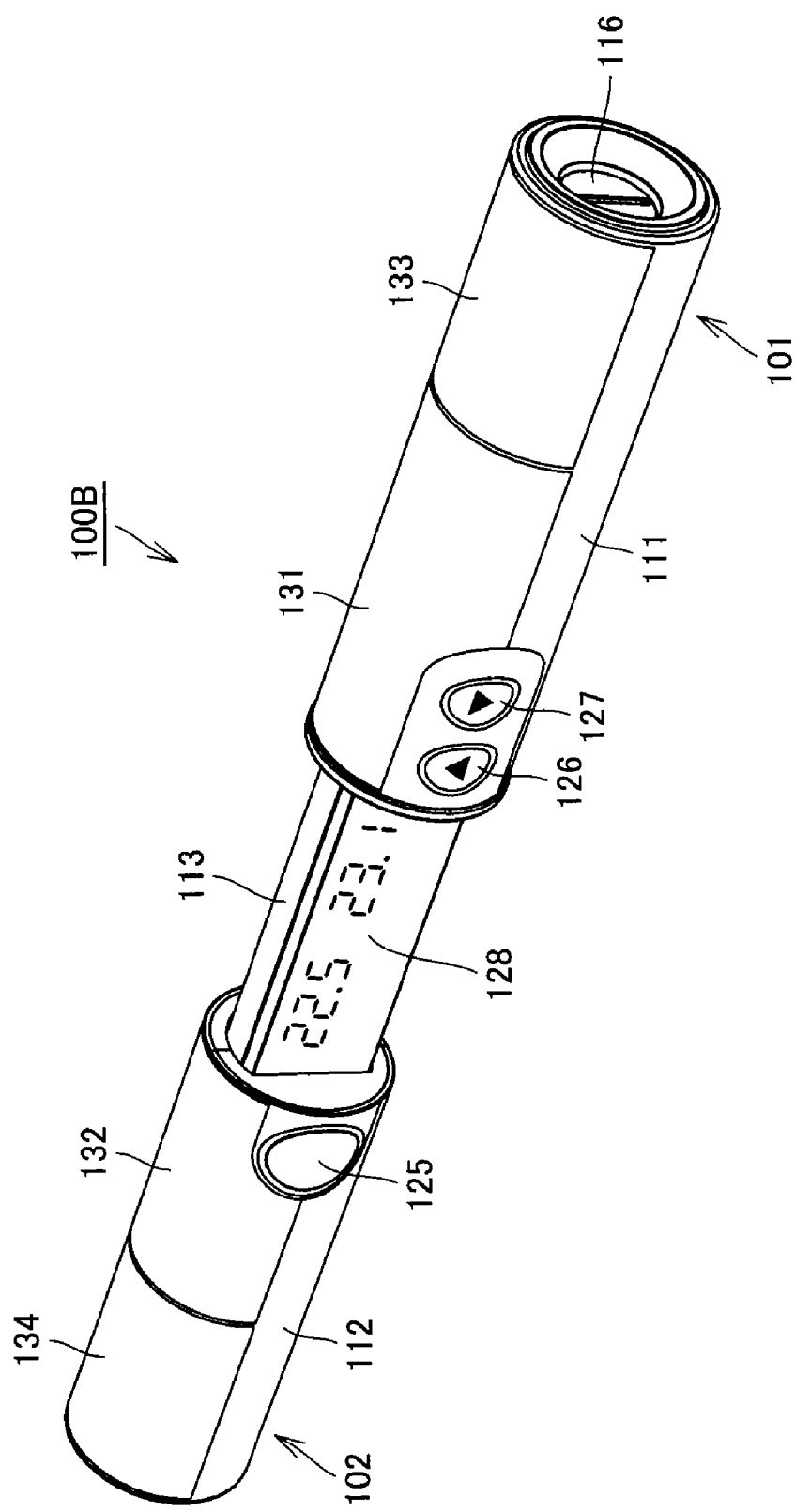
FIG. 11 is a perspective view showing the appearance of a body composition measuring apparatus in the measurable state in Embodiment 2 of the present invention.
Figure 12:
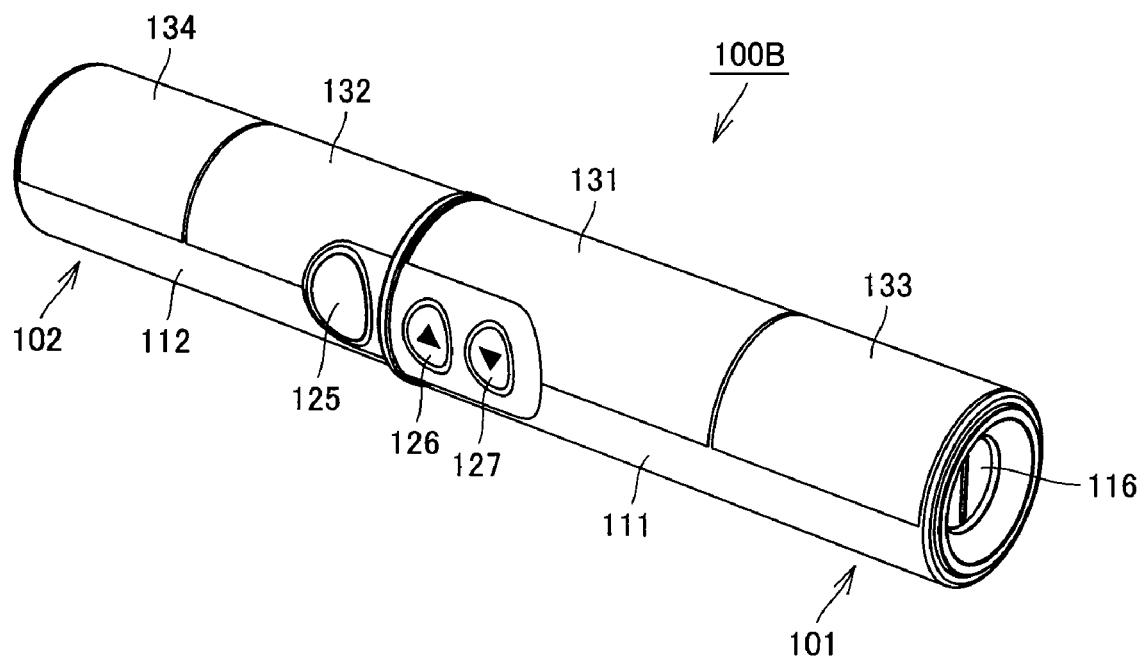
FIG. 12 is a perspective view showing the appearance of the body composition measuring apparatus in the storage state in Embodiment 2 of the present invention.

FIG. 11 is a perspective view showing the appearance of a body composition measuring apparatus in the measurable state in Embodiment 2 of the present invention. FIG. 12 is a perspective view showing the appearance of the body composition measuring apparatus in the storage state in the present embodiment. With reference to FIGS. 11 and 12, the appearance configuration of the body composition measuring apparatus in the present embodiment will first be described.

As shown in FIGS. 11 and 12, like body composition measuring apparatus 100A in the above embodiment, a body composition measuring apparatus 100B in the present embodiment has a substantially cylindrical outer shape, and includes a right hand grip 101 to be held with a right hand in the right end and a left hand grip 102 to be held with a left hand in the left end. A casing configuring the outer shell of the apparatus body of body composition measuring apparatus 100B is constituted by right casing 111, left casing 112, and central part casing 113, just as in body composition measuring apparatus 100A in the above embodiment. Central part casing 113 is disposed between right casing 111 and left casing 112 so as to bridge right casing 111 and left casing 112, and a display 128 is provided on the front surface of central part casing 113. Electrodes 131 and 133 are provided at predetermined positions on the outer surface of right casing 111, and electrodes 132 and 134 are provided at predetermined positions on the outer surface of left casing 112.

A measuring/setting button 125 for providing an instruction for starting measurement and performing various settings is disposed in a portion adjacent to display 128 of left casing 112, and an Up button 126 and a Down button 127 for selecting a value to be inputted, e.g., at the time of setting personal data are provided in a portion adjacent to display 128 in right casing 111. In body composition measuring apparatus 100B in the present embodiment, a power supply button, which is provided in body composition measuring apparatus 100A of Embodiment 1 described above, is not provided.

In body composition measuring apparatus 100B in the present embodiment, the power supply button is eliminated, and a detection portion that detects whether left casing 112 is at the measurable position is provided instead. This detection portion functions as a switch for supplying power to micon 141 when left casing 112 is at the measurable position. The configuration of this detection portion will be described in detail below.

Figure 13A:
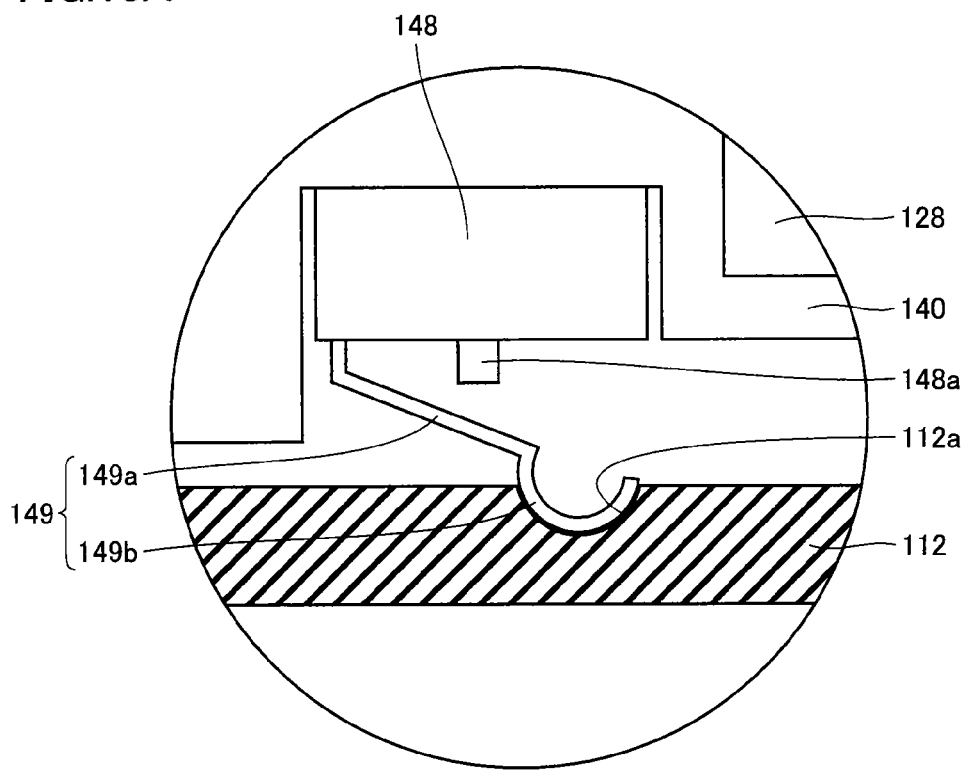
FIG. 13A is an enlarged cross-sectional view of the vicinity of a detection portion in the storage state, for describing the configuration of the detection portion of the body composition measuring apparatus in Embodiment 2 of the present invention.
Figure 13B:
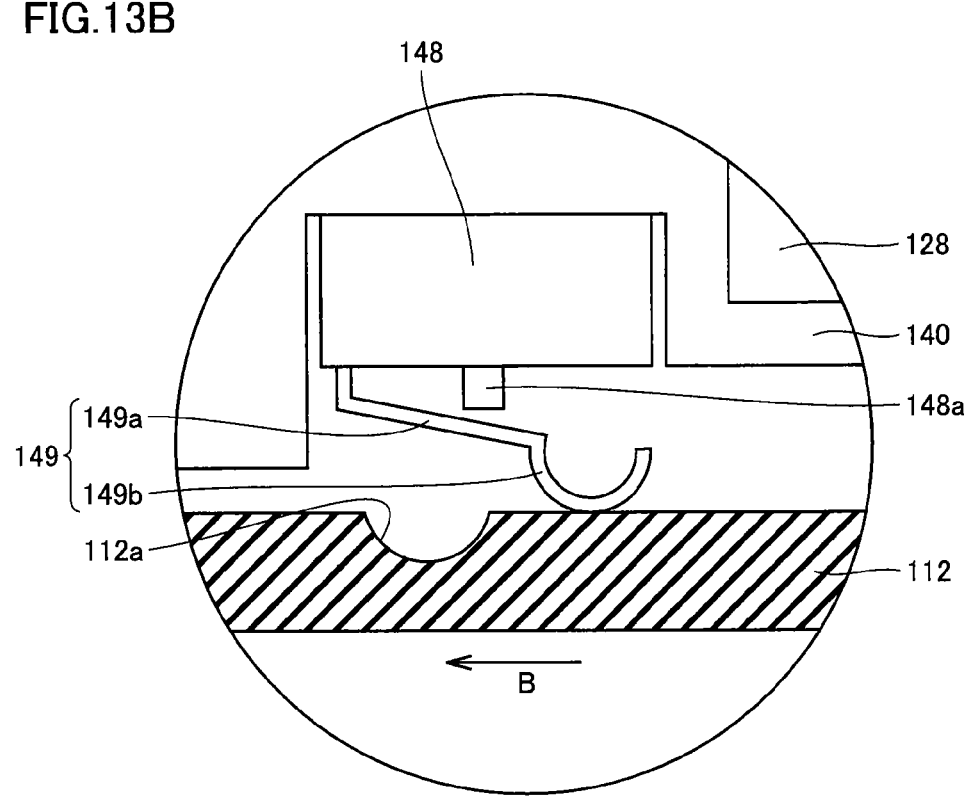
FIG. 13B is an enlarged cross-sectional view of the vicinity of the detection portion immediately after the storage state is released, for describing the configuration of the detection portion of the body composition measuring apparatus in Embodiment 2 of the present invention.
Figure 14A:
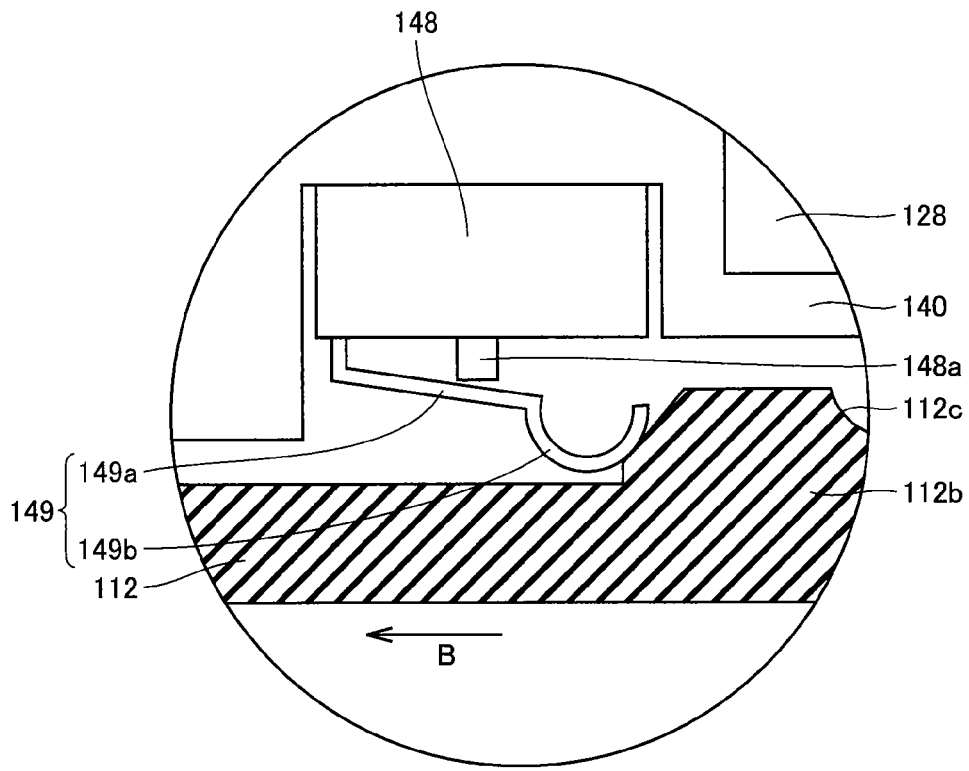
FIG. 14A is an enlarged cross-sectional view of the vicinity of the detection portion immediately before the measurable state is established, for describing the configuration of the detection portion of the body composition measuring apparatus in Embodiment 2 of the present invention.
Figure 14B:
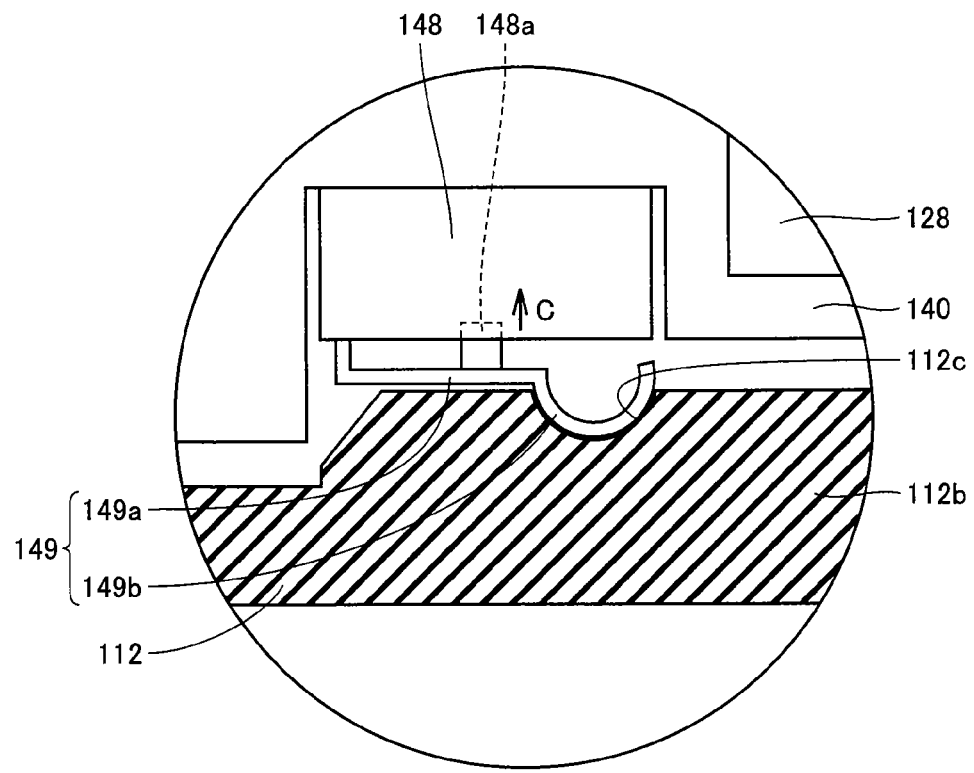
FIG. 14B is an enlarged cross-sectional view of the vicinity of the detection portion when the measurable state has been established, for describing the configuration of the detection portion of the body composition measuring apparatus in Embodiment 2 of the present invention.

FIGS. 13A, 13B, 14A, and 14B are figures for describing the configuration of the detection portion of body composition measuring apparatus in the present embodiment; FIG. 13A is an enlarged cross-sectional view of the vicinity of the detection portion in the storage state, FIG. 13B is an enlarged cross-sectional view of the vicinity of the detection portion immediately after the storage state is released, FIG. 14A is an enlarged cross-sectional view of the vicinity of the detection portion immediately before the measurable state is established, and FIG. 14B is an enlarged cross-sectional view of the vicinity of the detection portion when the measurable state has been established.

As shown in FIGS. 13A, 13B, 14A, and 14B, a switching unit 148 is attached to a predetermined position on circuit board 140, and a plate spring 149 as an engaging mechanism is attached to switching unit 148. Switching unit 148 has a switch 148a, and power is supplied in conjunction with the On/Off operations of this switch 148a. Plate spring 149 includes an elastic portion 149a extending linearly and an engaging portion 149b that is positioned at the tip of elastic portion 149a and has a curved shape, and switch 148a is arranged at a position corresponding to elastic portion 149a. Plate spring 149 is attached to switching unit 148 so as to exert biasing force toward the outside of circuit board 140.

On the other hand, as shown in FIGS. 13A and 13B, a concave 112a that can receive engaging portion 149b of plate spring 149 is provided at a predetermined position on the inner peripheral surface of left casing 112. As shown in FIG. 13A, with engaging portion 149b of plate spring 149 fixed into this concave 112a, engaging force acts between circuit board 140 and left casing 112 due to biasing force of elastic portion 149a. As a result, the movement of left casing 112 is limited. Accordingly, the storage state shown in FIG. 12 is maintained. Note that, in this state, switch 148a is in the off state.

However, as shown in FIG. 13B, if force is applied to left casing 112 in the arrow B direction in the figure by the subject, left casing 112 slidingly moves against the engaging force described above made by plate spring 149 and concave 112a. This causes engaging portion 149b of plate spring 149 to be disengaged from concave 112a. Thus, the storage state is released, thereby realizing smooth movement of left casing 112 with respect to right casing 111. Note that, in this state also, switch 148a is in the off state.

As shown in FIGS. 14A and 14B, a concave 112c that can receive engaging portion 149b of plate spring 149 is provided at a predetermined position of stopper 112b of left casing 112. By the foregoing operations of the subject, left casing 112 further moves in the arrow B direction shown in FIG. 14A. When engaging portion 149b of plate spring 149 reaches stopper 112b, engaging portion 149b of plate spring 149 gets over a tapered surface provided on stopper 112b. Then, as shown in FIG. 14B, engaging portion 149b of plate spring 149 is fixed into concave 112c provided in stopper 112b, and engaging force acts between circuit board 140 and left casing 112 due to biasing force of elastic portion 149a. As a result, the movement of left casing 112 is limited. Accordingly, the measurable state shown in FIG. 11 is maintained. In this state (i.e., in a state where engaging portion 149b of plate spring 149 has gotten over the tapered surface), switch 148a is pressed down in the arrow C direction in the figure by elastic portion 149a of plate spring 149 to be in the on state. In association therewith, power is supplied to micon 141.

Figure 15:
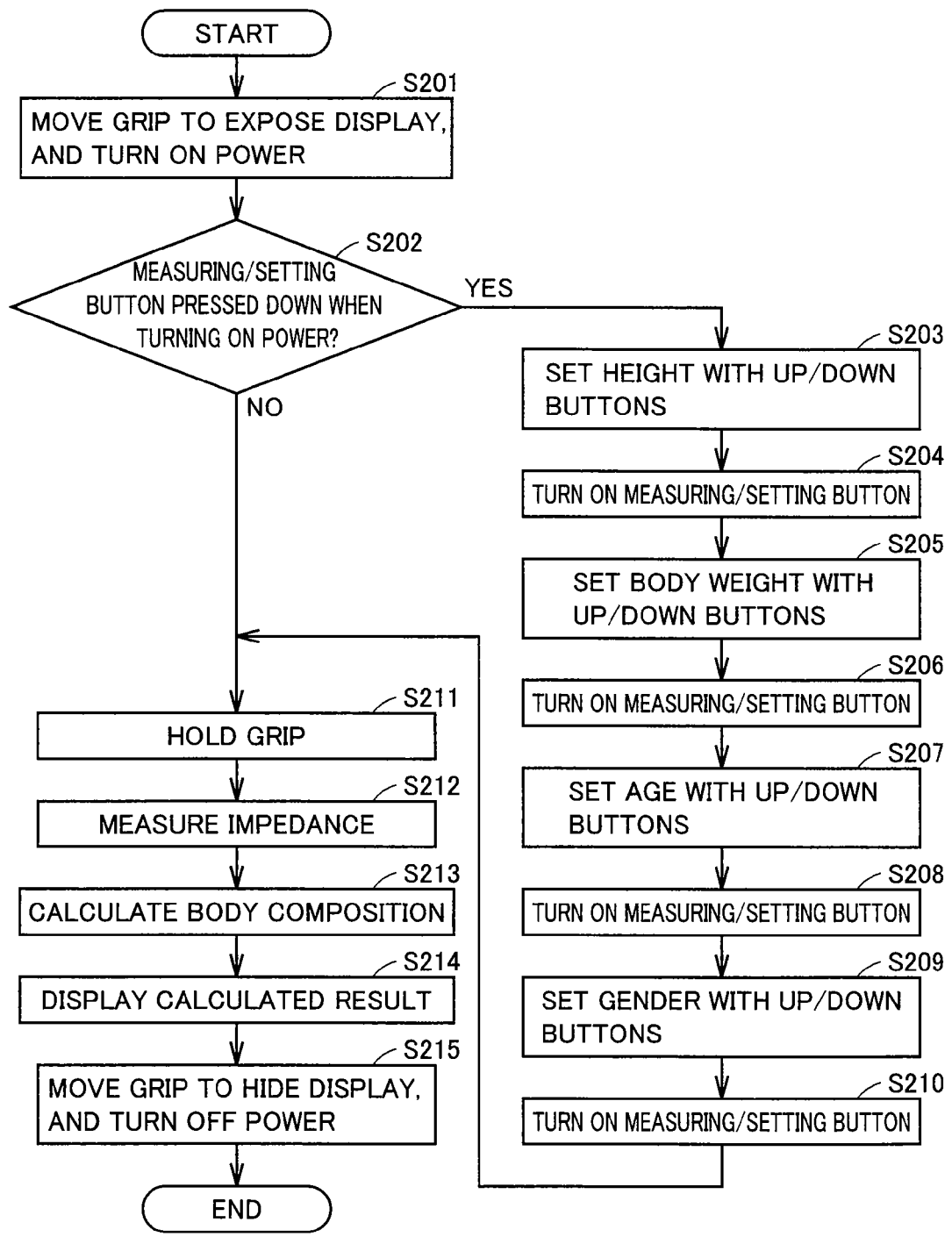
FIG. 15 is a flowchart in a case of measuring a body composition using the body composition measuring apparatus in Embodiment 2 of the present invention.

FIG. 15 is a flowchart in a case of measuring a body composition using the body composition measuring apparatus in the present embodiment. With reference to this figure, a flow when a body composition is measured will be described below.

As shown in FIG. 15, when a body composition is measured, first in step S201, left hand grip 102 is slidingly moved with respect to right hand grip 101 to expose display 128, thereby establishing the measurable state. At this point, switch 148a comes in the on state to supply power to micon 141. In body composition measuring apparatus 100B in the present embodiment, if measuring/setting button 125 is pressed down at the time of turning on the power, the process proceeds to a setting mode of personal data, whereas if measuring/setting button 125 is not pressed down at the time of turning on the power, the process proceeds to a measuring mode. Therefore, in step S202, it is determined whether measuring/setting button 125 is pressed down at the time of turning on the power. If the button is pressed down, then the process proceeds to step S203, while if the button is not pressed down, the process proceeds to step S211.

When the process proceeds to the setting mode of personal data, in steps S203 to S210, Up button 126 and Down button 127, and measuring/setting button 125 are operated to consecutively set personal data such as height, body weight, age, and gender.

When the process proceeds to the measuring mode and when the setting of personal data has been completed, after an interval of a predetermined time has passed by a timer circuit separately provided, impedance measurement is started. During this interval, the subject proceeds to step S211 and holds both grips 101 and 102 in the posture shown in FIG. 9. After the lapse of a predetermined time, in step S212, an impedance is measured; in step S213, a body composition is calculated; and in step S214, the calculated result of the body composition is displayed on display 128. When measurement is completed, in step S215, second grip 102 is slidingly moved with respect to right hand grip 101 to hide display 128, thereby establishing the storage state. At this point, switch 148a comes in the off state to stop the power supply to micon 141.

With this configuration, the need to press down the power supply button can be eliminated, and forgetting to turn off the power can be prevented. The need to press down the measuring start button can also be eliminated. Accordingly, a body composition measuring apparatus that can be easily handled can be obtained. Further, since a power supply button and a measuring start button need not be provided separately and independently, the apparatus configuration can be simplified. Thus, a small-sized body composition measuring apparatus can be obtained.

In Embodiments 1 and 2 described above, descriptions have been given by way of example of a case where the display is covered with the left casing constituting the second grip in the storage state. However, it is of course possible that the display is covered with the right casing constituting the first grip or with both the right and left casings in the storage state.

Further, in Embodiments 1 and 2 described above, descriptions have been given by way of example of a case where the right casing and the left casing are each formed of a cylindrical member. However, these casings are not necessarily cylindrical. So long as the member has a shape with a hollow formed inside, the shape is not limited to a cylindrical one.

It is to be understood that the foregoing embodiments disclosed herein are illustrative in all respects, and are not restrictive. It will be clear that technical scope of the present invention is defined by the following claims, and includes all changes and modifications within the scope and meaning of the description of claims and equivalents thereof.

The invention claimed is:

1. A body composition measuring apparatus comprising in a portable apparatus body:
   a first electrode to be contacted with one hand of a subject;
   a second electrode to be contacted with the other hand of the subject;

a measurement portion that measures an impedance of a body of the subject using said first electrode and said second electrode; and
a detection portion, wherein
said apparatus body includes:
a cylindrical first grip having said first electrode;
a cylindrical second grip having said second electrode; and
a display capable of displaying a body composition based on a measurement result measured by said measurement portion,
said first grip and said second grip are disposed such that respective axis lines thereof are disposed to overlap with each other on the same straight line,
said second grip is coupled, to be slidingly movable in a direction of the axis line thereof, to said first grip in a freely movable manner and is movable between a first position where measurement by said measurement portion is allowed by said body composition measuring apparatus and a second position where measurement by said measurement portion is not allowed by said body composition measuring apparatus,
said display is exposed in a state where said second grip is at said first position, and covered with at least one of said first grip and said second grip in a state where said second grip is at said second position, and
said detection portion is configured to detect whether said second grip is at said first position, and detection by said detection portion that said second grip is at said first position causes power to be supplied to said measurement portion.

2. The body composition measuring apparatus according to claim 1, wherein
said first position is a position where said second grip is, in a movable range thereof, remotest from said first grip, and
said second position is a position where said second grip is, in a movable range thereof, closest to said first grip.

3. The body composition measuring apparatus according to claim 2, wherein a length in said axis line direction of said apparatus body when said second grip is at said second position is smaller than a length in said axis line direction of said apparatus body when said second grip is at said first position.

4. The body composition measuring apparatus according to claim 1, further comprising an engaging mechanism capable of engaging said second grip at said first position and at said second position.

5. The body composition measuring apparatus according to claim 1, wherein when power is supplied to said measurement portion, measurement by said measurement portion is started immediately or after the lapse of a predetermined time.

6. The body composition measuring apparatus according to claim 1, further comprising a detection portion that detects whether said second grip is at said first position, wherein
detection by said detection portion that said second grip is not at said first position causes power supply to said measurement portion to be stopped.

7. A body composition measuring apparatus comprising in a portable apparatus body:
a first electrode to be contacted with one hand of a subject;
a second electrode to be contacted with the other hand of the subject; and
a measurement portion that measures an impedance of a body of the subject using said first electrode and said second electrode, wherein
said apparatus body includes:
a cylindrical first grip having said first electrode;
a cylindrical second grip having said second electrode;
a display capable of displaying a body composition based on a measurement result measured by said measurement portion; and
an operating portion,
said first grip and said second grip are disposed such that respective axis lines thereof are disposed to overlap with each other on the same straight line,
said second grip is coupled, to be slidingly movable in a direction of the axis line thereof, to said first grip in a freely movable manner and is movable between a first position where measurement by said measurement portion is allowed by said body composition measuring apparatus and a second position where measurement by said measurement portion is not allowed by said body composition measuring apparatus,
said display is exposed in a state where said second grip is at said first position, and covered with at least one of said first grip and said second grip in a state where said second grip is at said second position, and
said operating portion is provided on at least one of said cylindrical first grip and said cylindrical second grip and is configured to receive instructions from said subject to operate said body composition measuring apparatus.

8. The body composition measuring apparatus according to claim 7, wherein
said first position is a position where said second grip is, in a movable range thereof, remotest from said first grip, and
said second position is a position where said second grip is, in a movable range thereof, closest to said first grip.

9. The body composition measuring apparatus according to claim 8, wherein a length in said axis line direction of said apparatus body when said second grip is at said second position is smaller than a length in said axis line direction of said apparatus body when said second grip is at said first position.

10. The body composition measuring apparatus according to claim 7, further comprising an engaging mechanism capable of engaging said second grip at said first position and at said second position.

11. The body composition measuring apparatus according to claim 7, further comprising a detection portion that detects whether said second grip is at said first position, wherein
detection by said detection portion that said second grip is at said first position causes power to be supplied to said measurement portion.

12. The body composition measuring apparatus according to claim 11, wherein when power is supplied to said measurement portion, measurement by said measurement portion is started immediately or after the lapse of a predetermined time.

13. The body composition measuring apparatus according to claim 7, further comprising a detection portion that detects whether said second grip is at said first position, wherein
detection by said detection portion that said second grip is not at said first position causes power supply to said measurement portion to be stopped.

14. The body composition measuring apparatus according to claim 7, wherein said operating portion comprises a button.

15. The body composition measuring apparatus according to claim 7, wherein said operating portion comprises a dial.

* * * * *